United States Patent [19]
Muizzuddin et al.

[11] Patent Number: 5,958,976
[45] Date of Patent: Sep. 28, 1999

[54] COMPOSITION AND METHOD FOR REDUCING STINGING IN SKIN

[75] Inventors: Neelam Muizzuddin, Bethpage; Kenneth D. Marenus, Dix Hills; Glen Rein, Miller Place, all of N.Y.; Mary Steidl Matsui, Teaneck, N.J.

[73] Assignee: E-L Management Corp., New York, N.Y.

[21] Appl. No.: 08/933,571

[22] Filed: Sep. 19, 1997

[51] Int. Cl.⁶ ..................................... A61K 31/195
[52] U.S. Cl. ............................................. 514/561
[58] Field of Search ............................................. 514/561

[56] References Cited

U.S. PATENT DOCUMENTS 3,970,748   7/1976   Mecca .

FOREIGN PATENT DOCUMENTS

| 44299289 | of 1995 | Germany . |
| 60-036413 | 2/1985 | Japan . |
| 6145038 | 5/1994 | Japan . |
| WO 95/15147 | 6/1995 | WIPO . |

OTHER PUBLICATIONS

Han Faming Zhuanli Shenqing Gonkai Shuomingshu, 4 pp (China) (Abstract) 1993.

Chemical Abstracts vol. 118: 241882z (Hasunuma et al) 1993.

Chemical Abstracts vol. 122: 38511t(Chikamatsu et al) 1995.

L–glutamine Inhibits Nitric Oxide Synthesis in Bovine Venular Endothelial Cells, Meininger, et al., J Pharmacol Exp Ther, Apr., 1997 281:1, 448–53 (Abstract).

Identification of a System N–like Na($^+$)–dependent Glutamine Transport Activity in Rat Brain Neurons Tamarapoo, et al.,J Neurochem, Mar., 1997 68:3,954–60 (Abstract).

Peptides Containing Glutamine Repeats as Substrates for Transglutaminase–Catalyzed Cross–Linking: Relevance to Diseases of the Nervous System, Kahlem, et al., Proc Natl Acad Sci USA, Dec. 10, 1996 93:25, 14580–5 (Abstract).

The Emerging Role of Glutamine as an Indicator of Exercise Stress and Overtraining, Rowbottom, et al. Sports Med, Feb., 1966 21:2, 80–97 (Abstract).

Glutamine, Hall et al., Br J. Surg, Mar., 1966 83:3, 305–12 (Abstract).

Glutamate and Glutamine Metabolism in Cultured GABAergic Neurons Studied by 13C NMR Spectroscopy May Indicate Compartmentation and Metochondrial Heterogeneity, Westergaard, et al., Neurosci Lett, Feb. 6, 1955 185:1, 24–8 (Abstract).

The Role of Glutamate and GABA Receptors in the Generation of Dorsal Root Reflexes by Acute Arthritis in the Anaesthetized Rat, Rees, et al.,J Physiol (London)Apr. 15, 1995, 484 (Pt 2) p. 437–45, ISSN (Abstract).

Inflammation–Induced Release of Excitatory Amino Acids is Prevented by Spinal Administration of a GABAA but not by a GABAB Receptor Antagonist in Rats, Sluka, et al., J Pharmacol Exp Ther (US), Oct. 1994, 271 (1) p. 76–82, ISSN 0022–3565 Journal Code: JP3 (Abstract).

A Method for Appraising the Stinging Capacity of Topically Applied Substances, Peter J. Frosch et al. J. Soc. Cosmet. Chem., 28, 197–209 (May 1977).

*Primary Examiner*—Raymond Henley, III
*Attorney, Agent, or Firm*—Karen A. Lowney, Esq.

[57] ABSTRACT

The invention relates to topical cosmetic or pharmaceutical compositions comprising an anti-stinging effective amount of an amino acid selected from the group consisting of an amino butyric acid, glutamine, glycine, and derivatives thereof, or mixtures thereof, as well as methods of reducing or preventing stinging using such compositions.

10 Claims, No Drawings

COMPOSITION AND METHOD FOR REDUCING STINGING IN SKIN

FIELD OF THE INVENTION

The invention relates to cosmetic and therapeutic compositions useful in alleviating the symptoms of irritation or stinging which occur on the skin spontaneously or with the application of topical products. More specifically, the invention relates to a composition containing one or more materials which reduce or eliminate unpleasant neurosensory responses, such as the stinging that occurs, for example, with application of lactic acid to the skin.

BACKGROUND OF THE INVENTION

It is not uncommon to hear many individuals assert that they have unusually sensitive skin. In such cases, the afflicted individual frequently reports itching, burning or stinging as the result of an identifiable event, such as applying a specific material to the skin; however, a similar reaction may also be reported as a response to a non-specific environmental stimulus. In either case, the reaction causes significant, and regular, discomfort to those individuals so afflicted.

In the case of a specific product causing the stinging reaction, the stinging potential of the product is frequently not even apparent upon initial testing. It is not uncommon that a product for topical application will pass all standard tests for topical safety, yet when in general distribution, the product will elicit a number of complaints from a substantial percentage of users. Those who report "subjective" stinging exhibit no objectively observable physical symptoms upon exposure to certain types of external stimuli, yet consistently and reliably report discomfort upon such exposure. It is now generally accepted that there is a fairly sizable subpopulation within the general population who can be defined as "stingers", i.e., who have a very delicate or hypersensitive skin (Frosch and Kligman, J. Soc. Cosm. Chem. 28: 197, 1977). The phenomenon is frequently referred to as "lactic acid stinging", in reference to the substance that is frequently used to elicit this reaction in objective testing so as to identify sensitive individuals. The physiological basis for this response is at the present time still a mystery. However, there appear to be no reliable phenotypic indicia which permit the a priori identification of "stingers" in the population.

The stinging problem is clearly one that affects both the consumer and the manufacturers of topically applied products. The highly sensitive consumer is often deprived of the benefits of many useful products because of the irritation experienced upon use. The manufacturer in turn is hampered by the necessity for extensive, and expensive, testing to identify materials in formulation which may cause stinging, and even then, will be unable to identify that small, but significant, subpopulation of users who will be affected by potentially stinging material. Thus, considerable research and development efforts may be invested in a product which will be unusable by a substantial percentage of the intended users. It would, therefore, be beneficial to determine a means by which the stinging potential of certain products can be reduced, and/or by which the stinging subset of the population can be treated to reduce the propensity to stinging. The present invention provides such a means.

SUMMARY OF THE INVENTION

The present invention relates to cosmetic and pharmaceutical compositions for topical application to skin comprising effective amounts of at least one of the amino acids selected from glutamine, an amino butyric acid, and glycine, in a cosmetically or pharmaceutically acceptable carrier. The invention also relates to compositions comprising at least one of the amino acids selected from glutamine, an amino butyric acid, and glycine, in combination with at least one active agent which is known to cause stinging on the skin, in a cosmetically or pharmaceutically acceptable carrier. The invention further encompasses a method for the prevention or alleviation of stinging on the skin due to the presence of a stinging agent on the skin, which comprises applying to the skin effective amounts of at least one of the amino acids selected from glutamine, an amino butyric acid, and glycine, either before, simultaneously with, or subsequent to exposure to the stinging agent. The invention also relates to a method for reducing the sensitivity of the skin of an individual susceptible to lactic acid stinging which comprises applying to the skin of the individual an effective amount of at least one of the amino acids selected from glutamine, an amino butyric acid, and glycine.

DETAILED DESCRIPTION OF THE INVENTION

The invention is based on the observation that each of glycine, glutamine and an amino butyric acid, when applied in effective amounts to skin of individuals exposed to a stinging agent, significantly reduce the perception of stinging in those individuals. All the active agents of the invention are amino acids which have other known biological activities. For example, gamma amino butyric acid (GABA) is the principle inhibitory neurotransmitter in the mammalian central nervous system; similarly, glutamine and glycine have also been shown to play roles in neurotransmission, also in the central nervous system. In addition, GABA and various derivatives thereof have been known for their antiinflammatory effect when administered non-topically. However, none of these compounds, either alone or in combination with each other, has been previously shown to have any effect on neurotransmission in the peripheral nervous system, and further, none has been shown be able to prevent or reduce the lactic acid stinging response by topical application to the skin.

As used herein, the terms "amino butyric acid", "glutamine", and "glycine", throughout the specification and claims, refer not only to the named amino acid per se, but also to derivatives and analogs thereof which possess the same inhibitory properties. For example, each term also encompasses salts, esters, and amides of the amino acid. Derivatives/analogs of the amino acids can be confirmed for this activity by analysis in the stinging test protocol as described herein in the examples below. In a preferred embodiment, the amino butyric acid is gamma amino butyric acid, and the glutamine is N-acetyl glutamine. The concentration of the compound used may vary, but will generally be in the range of from about 0.1–20%, preferably from about 0.5–10%, and more preferably from about 0.05–3% of any one component. The individual amino acids, or derivatives or analogs, can also be combined in a single formulation. In one embodiment, GABA, glycine and N-acetyl glutamine are combined in an amount of from about 0.1–10%, preferably about 0.5–3%, of each component.

The active amino acids of the invention can be formulated in any cosmetically or pharmaceutically acceptable vehicle. The term "pharmaceutically or cosmetically acceptable carrier" refers to a vehicle, for either pharmaceutical or cosmetic use, which vehicle delivers the active component to the intended target and which will not cause harm to humans or other recipient organisms. As used herein, "pharmaceutical" or "cosmetic" will be understood to encompass both human and animal pharmaceuticals or cosmetics. The carrier may be in any form appropriate to the mode of delivery, for example, solutions, colloidal dispersions, emulsions, suspensions, creams, lotions, gels, foams, mousses and the like. The formulations preferably have a pH of about 5–8.

The formulations containing the amino acid(s) are used to prevent or reduce the stinging caused by various stinging agents.

The formulations containing the amino acid(s) are used to prevent or reduce the stinging caused by various stinging agents. As used throughout the specification and claims, a "stinging agent" is one which elicits a positive response when tested on a group of individuals with a history of stinging; methodology for determination of propensity for lactic acid stinging is described, for example, in Frosch and Kligman, J. Soc. Cosm. Chem. 28: 197, 1977, the contents of which are incorporated herein by reference in its entirety, or as in the examples below. Thus, the identity of a stinging agent may be determined on an ad hoc basis. However, there are also a number of known agents frequently used in skin treatment which have historically been identified as causing a subjective stinging reaction of the skin. An exemplary list is provided in Frosch and Kligman, supra, and include such commonly used materials as retinoids, Vitamin C, hydroxy acids, e.g., lactic, citric or salicylic acids, and propylene glycol. The amino acids of the invention can be used in a combined treatment regimen with any agent which induces subjective, or lactic acid-type, of stinging.

The timing of application of the amino acid-containing composition of the invention can be varied. The amino acid(s) can be applied before contact with a stinging agent, for example, as much as 30 minutes before, to prevent or reduce the effect of an agent to be applied shortly thereafter; an example of such application would be in connection with a planned treatment of the skin with a retinoid or hydroxy acid, or other irritating therapeutic agent. Similarly, the amino acid(s) can also be applied shortly after contact with a stinging agent, to alleviate a stinging reaction; in addition to such application with planned application of irritating therapeutic agents, this subsequent application of the amino acids can be used in connection with an unanticipated, or single occurrence stinging event, e.g., an insect sting or bite, a contact dermatitis, or the stinging insect sting or bite, a contact dermatitis, or the stinging occasionally encountered with shaving the skin. In an alternate embodiment, the amino acid(s) is combined directly with the stinging agent in the same formulation, to provide a simultaneous application of the agent with the remedy.

The amino acids can also be applied as long as several weeks before contact with a stinging agent. In connection with the latter application regimen, the amino acid formulation can essentially be used as a general skin-desensitizer, i.e., to reduce the overall sensitivity of the skin, in anticipation of a non-specific encounter with a stinging agent. This has particular application in preventing or reducing the response that many individuals have to irritating environmental stimuli, such as smoke, dust, or pollution, or even to stimuli which are non-specific or unidentifiable, but which result in an irritation response in the skin of sensitive individuals. For this type of use, the amino acid composition is applied in a regular pattern, preferably at least daily, more preferably twice daily, to "prime" the skin, and render it less susceptible to stinging when the encounter with a stinging agent occurs.

The invention is further illustrated by the following non-limiting examples.

EXAMPLES

I. An oil-in-water emulsion containing one of the amino acids of the invention is prepared as follows:

| Material | Weight % |
|---|---|
| Oil phase | |
| stearic Acid | 2.40 |
| glyceryl monostearate | 2.20 |
| butyl paraben | 0.10 |
| mineral oil/lanolin alcohol | 9.55 |
| petrolatum/lanolin alcohol | 2.00 |
| sesame oil | 4.30 |
| propyl paraben | 0.10 |
| Water phase | |
| deionized water | 72.83 |
| triethanolamine | 0.82 |
| methyl paraben | 0.30 |
| trisodium EDTA | 0.10 |
| propylene glycol | 4.30 |
| amino acid | 1.00 |

II. Three individual oil-in-water formulations, as described in Example I, are prepared containing (1)1% glycine; (2)1% N-acetyl glutamine; or (3)1% GABA, and used as test treatments in a clinical study.

A total of 30 female volunteers between the ages of 18–45 are tested in the complete study. All subjects chosen have a history of lactic acid stinging, but otherwise are of normal health, with no evidence of acute or chronic disease, including dermatologic or ophthalmic problems. Individuals with current sunburn, rashes, scratches, burn marks, etc. which might interfere with the evaluation of the test results are excluded.

A. Single application. The panel is divided in three groups of 10, corresponding to each product. Ten percent lactic acid is applied on one side of the face and saline on the other side (Frosch and Kligman, supra) Sting intensity as reported by the panelists is documented after 2.5 minutes and 5 minutes. Cumulative sting intensity is calculated.

The following day, each test product is applied on the face with special emphasis on the nasolabial fold. The product is allowed to absorb for 30 minutes, and then 10% lactic acid is applied on one side of the face and saline on the other side. Sting intensity as reported by the panelists is documented after 2.5 and 5 minutes. Cumulative sting intensity is calculated.

B. Multiple applications. The same panelists are provided with the products to be applied on full face twice a day for 4 weeks. After 1 month of treatment, the panelists are tested again. On the day of the test, the panelists do not apply the product. Ten percent lactic acid is applied on one side of the face and saline on the other side. Sting intensity as reported by the panelists is documented after 2.5 minutes and 5 minutes. Cumulative sting intensity is calculated at each time point. The difference between the sting intensity of baseline versus 4 week treatment is calculated.

The results of both studies are depicted graphically in FIG. 1. The graph shows that all test products are very effective in reducing lactic acid stinging after a single treatment, as follows, in % reduction of stinging: N-acetyl glutamine, 53%; GABA, 56%; glycine, 70%. However, varying results are observed after one month of treatment.

The glutamine-containing product is considerably less active after one month treatment (18% reduction of stinging), exhibiting little or no accumulation of activity over time. The GABA product is effective after 4 weeks of treatment, with a 47% reduction in stinging observed. The glycine product performs best, with a 63% reduction in stinging after the multiple application treatment.

What we claim is:

1. A method for reducing stinging on the skin caused by the skin's contact with a stinging agent which comprises applying to the skin an anti-stinging effective amount of an amino acid selected from the group consisting of an amino butyric acid, glutamine, glycine, and derivatives thereof, or mixtures thereof.

2. The method of claim 1 in which the amino acid is glycine.

3. The method of claim 1 in which the amino acid is gamma-amino butyric acid.

4. The method of claim 1 in which the amino acid is N-acetyl glutamine.

5. The method of claim 1 in which the stinging is lactic acid-type stinging.

6. The method of claim 1 in which the amino acid is applied before contact with the stinging agent.

7. The method of claim 1 in which the amino acid is applied substantially simultaneously with the stinging agent.

8. The method of claim 1 in which the amino acid is applied after the stinging agent.

9. The method of claim 8 in which the stinging agent is an insect sting or bite.

10. The method of claim 1 in which the amino acid is applied daily.

* * * * *